United States Patent [19]

Oppenheim et al.

[11] Patent Number: 5,696,078
[45] Date of Patent: Dec. 9, 1997

[54] METHODS OF TREATING FUNGAL INFECTIONS USING HISTATIN-BASED PEPTIDES

[75] Inventors: Frank G. Oppenheim, Chestnut Hill; Tao Xu, Somerville, both of Mass.

[73] Assignee: The Trustees of Boston University, Boston, Mass.

[21] Appl. No.: 441,914

[22] Filed: May 16, 1995

Related U.S. Application Data

[62] Division of Ser. No. 287,717, Aug. 9, 1994, Pat. No. 5,486,503, which is a continuation of Ser. No. 145,030, Oct. 28, 1993, abandoned, which is a continuation of Ser. No. 786,571, Nov. 1, 1991, abandoned.

[51] Int. Cl.$^6$ ............................................. A61K 31/00
[52] U.S. Cl. .................. 514/2; 424/405; 424/430; 424/435; 424/443; 424/484; 530/327; 530/326; 530/325; 530/324
[58] Field of Search .............................. 424/405, 430, 424/435, 443, 484; 514/2

[56] References Cited

U.S. PATENT DOCUMENTS

| | | | |
|---|---|---|---|
| 4,705,777 | 11/1987 | Lehrer et al. | 514/12 |
| 4,725,576 | 2/1988 | Pollock et al. | 530/326 |
| 5,032,574 | 7/1991 | Wilde et al. | 514/12 |
| 5,126,257 | 6/1992 | Gabay et al. | 435/212 |
| 5,221,732 | 6/1993 | Chen et al. | 530/326 |
| 5,225,399 | 7/1993 | Zasloff et al. | 514/13 |
| 5,239,059 | 8/1993 | Zasloff et al. | 530/325 |
| 5,304,633 | 4/1994 | Tomita et al. | 530/326 |
| 5,324,716 | 6/1994 | Selsted et al. | 514/14 |

OTHER PUBLICATIONS

Oppenheim, F.G. et al., "Isolation and Characterization of a Major Histatin from Macaque Parotid Secretion," *FASEB J.* 4(7): A2165 (Apr. 1990).

Xu, T. and Oppenheim, F.G., "Structure/Function Analysis of Anti-Candida Activities of Histatin 1," *J. Dent. Res.* 68: 973 (Jun. 1989).

Oppenheim, F.G. et al., "Histatins, A Novel Family of Histidine-Rich Proteins in Human Parotid Secretion," *J. Biol. Chem.* 263(16): 742-777 (Jun. 5, 1988).

Troxler, R.F. et al., "Structural Relationship between Human Salivary Histatins," *J. Dent. Res.* 69(1): 2-6 (Jan. 1990).

Santarpia III, R.P. et al., "Preliminary Findings for in vivo Efficacy of Salivary Histadine-Rich Polypeptides," *J. Dent. Res.* 69: 173 (Mar. 1990).

Iwaki, M. et al., "Oral Immunization with Recombinant *Streptococcus lactis* Carrying the *Streptococcus mutans* Surface Protein Antigen Gene," *Infect. Immun.* 58(9): 2929-2934 (Sep. 1990).

Macrina, F.L. et al., "Chimeric Streptococcal Plasmids and Their Use as Molecular Cloning Vehicles in *Streptococcus sanguis* (Challis)," *J. Bacteriol.* 143(3): 1425-1435 (Sep. 1980).

Kuramitsu, H.K. and Long, C.M., "Plasmid-Mediated Transformation of *Streptococcus mutans*," *Infect. Immun.* 36(1): 435-436 (Apr. 1982).

(List continued on next page.)

*Primary Examiner*—Robert A. Wax
*Assistant Examiner*—William W. Moore
*Attorney, Agent, or Firm*—Hamilton, Brook, Smith & Reynolds, P.C.

[57] ABSTRACT

Peptides representing defined portions of the amino acid sequences of naturally occurring human and macaque histatins, modified peptides, expression vectors encoding these peptides, and compositions and methods for treatment of fungal infection are described. Some of the histatin-based peptides exhibit superior anti-fungal activity to native, intact histatins. Isolated, naturally occurring macaque histatins and peptide analogs are also described.

3 Claims, 9 Drawing Sheets

OTHER PUBLICATIONS

Svanberg, M. et al., "Oral Implantation in Humans of *Streptococcus mutans* Strains with Different Degrees of Hydrophobicity," *Infect. Immun.* 43(3): 817–821 (Mar. 1984).

Docherty, J.J. and Pollock, J.J., "Inactivation of Herpes Simplex Virus Types 1 and 2 by Synthetic Histidine Peptides," *Antimicrobial Agents and Chemotherapy* 31(10): 1562–1566 (Oct. 1987).

Nishikata, M. et al., "Salivary Histatin as an Inhibitor of a Protease Produced by the Oral Bacterium *Bacteroides gingivalis*," *Biochem. Biophys. Res. Comm.* 174(2): 625–630 (Jan. 31, 1991).

Xu, T. et al., "Primary Structure and Anti-Candidal Activity of the Major Histatin from Parotid Secretion of the Subhuman Primate *Macaca fascicularis*," *J. Dent. Res.* 69: 1717–1723 (Nov. 1990).

Xu, T. and Oppenheim, F.G., "Anti-Fungal Functional Domain of Histatin 3," *J. Dent. Res.* 70: 497 (Apr. 1991).

Xu, T. et al., "Anticandidal Activity of Major Human Salivery Histatins," *Infect. Immun.* 59(8): 2549–2554 (Aug. 1991).

Raj, P.A. et al., "Salivary Histatin 5: Dependence of Sequence, Chain Length, and Helical Conformation for Candidacidal Activity," *J. of Biol. Chem.* 265(7): 3898–3905 (Mar. 5, 1990).

Murakami, Y. et al., "Inhibitory Effects of Synthetic Histidine-Rich Peptides on Haemagglutination by *Bacteroides gingivalis* 381," *Archives of Oral Biol.* 35(9): 775–777 (1990).

Minaguchi, K. and A. Bennick, "Genetics of Human Salivary Proteins," *J. Dent. Res.* 68(1): 2–15 (Jan., 1989).

Santarpia III, R.P. et al., "A Comparison of the Inhibition of Blastospore Viability and Germ-Tube Development in *Candida albicans* by Histidine Peptides and Ketoconazole," *Archives of Oral Biol.* 33(8): 567–573 (1988).

vanderSpek, J.C. et al., "Localization of the Genes for Histatins to Human Chromosome 4q13 and Tissue Distribution of the mRNAs," *Am. J. Hum. Genet.* 45: 381–387 (1989).

Sabatini, L.M. et al., "Tissue Distribution of RNAs for Cystatins, Histatins, Statherin, and Proline-rich Salivary Proteins in Humans and Macaques," *J. of Dental Res.* 68(7): 1138–1145 (Jul., 1989).

vanderSpek, J.C. et al., "Molecular Cloning of Human Submandibular Histatines," *Archives of Oral Biol.*, 35(2): 137–143 (1990).

Sabatini, L.M. et al., "Tissue Distribution of RNAs for Salivary-Type Proteins in Humans and Monkeys: Proline-rich Proteins, Statherin, Cystatins, and Histidine-rich Proteins," *Am. J. of Human Genetics* 43(3rd Supplement) A199 (Abstract) (1988).

Sugiyama, K. et al., "Rapid Purification and Characterization of Histatins (Histidine-Rich Polypeptides) from Human Whole Saliva," *Archives of Oral Biol.* 35(6)415–419 (1990).

Dickinson, D.P. et al., "Human Submandibular Gland Statherin and Basic Histidine-rich Peptide are Encoded by Highly Abundant mRNA's Derived from a Common Ancestral Sequence," *Biochem. and Biophys. Res. Comm.* (149(2): 784–790 (Dec. 16, 1987).

Sabatini, L.M. et al., "Histatins, A Family of Salivary Histidine-Rich Proteins, are Encoded by at Lease Two Loci (His 1 and His 2)," *Biophys. Res. Communications* 160(2): 495–502 (1989).

FIG. 1

```
                   1               5                   10                  15                  20
Histatin 3    Asp-Ser-His-Ala-Lys-Arg-His-His-Gly-Tyr-Lys-Arg-Lys-Phe-His-Glu-Lys-His-His-Ser-
SPM-H3                                                Arg-Lys-Phe-His-Glu-Lys-His-His-Ser-
3P1                           Lys-Arg-His-His-Gly-Tyr-Lys-Arg-Lys-Phe-His-Glu-Lys-His-His-Ser-
3P2                                       Gly-Tyr-Lys-Arg-Lys-Phe-His-Glu-Lys-His-His-Ser-
3P3                           Lys-Arg-His-His-Gly-Tyr-Lys-Arg-Lys-Phe-His-Glu-Lys-His-His-Ser-
3P4                                       Gly-Tyr-Lys-Arg-Lys-Phe-His-Glu-Lys-His-His-Ser-
3P5                           Lys-Arg-His-His-Gly-Tyr-Lys-Arg-Lys-Phe-His-Glu-Lys-His-His 21                      25                      30
Histatin 3    His-Arg-Gly-Tyr-Arg-Ser-Asn-Tyr-Leu-Tyr-Asp-Asn
SPM-H3        His-Arg-Gly-Tyr-Arg
3P1           His-Arg-Gly-Tyr-Arg
3P2           His-Arg-Gly-Tyr-Arg
3P3           His-Arg
3P4           His-Arg
```

FIG. 5

```
              1                                                        20
M-histatin 1: Asp-Pse-His-Glu-Glu-Arg-His-His-Gly-Arg-His-Gly-His-His-Lys-Tyr-Gly-Arg-Lys-Phe-His-Glu-Lys- Histatin 1:   Asp-Pse-His-Glu-Lys-Arg-His-His-Gly-------------------Tyr-Arg-Arg-Lys-Phe-His-Glu-Lys- Histatin 3:   Asp-Pse-His-Ala-Lys-Arg-His-His-Gly-------------------Tyr-Lys-Arg-Lys-Phe-His-Glu-Lys- 24                                   30                              38
              His-His-Ser-His-Arg-Gly-------------------Tyr-Arg-Ser-Asn-Tyr-Leu-Tyr-Asp-Asn His-His-Ser-His-Arg-Glu-Phe-Pro-Phe-Tyr-Gly-Asp-Tyr-Gly-Ser-Asn-Tyr-Leu-Tyr-Asp-Asn His-His-Ser-His-Arg-Gly-----------------------Tyr-Arg-Ser-Asn-Tyr-Leu-Tyr-Asp-Asn
```

FIG. 6

```
              1                   5                  10                 15                  20
M-histatin 1  Asp-Ser-His-Glu-Glu-Arg-His-His-Gly-Arg- His-Gly-His-His-Lys-Tyr-Gly-Arg-Lys-Phe-
SPM-MHa                                          Arg- His-Gly-His-His-Lys-Tyr-Gly-Arg-Lys-Phe-
SPM-MHb                                          Arg- His-Gly-His-His-Lys-Tyr-Gly-Arg-Lys-Phe-
SPM-MHc                                          Arg- His-Gly-His-His-Lys-Tyr-Gly-Arg-Lys-Phe- 25                  30                 35
M-histatin 1  His-Glu-Lys-His-His-Ser-His-Arg-Gly-Tyr-Arg-Ser-Asn-Tyr-Leu-Tyr-Asp-Asn
SPM-MHa       His-Glu-Lys-His-His-Ser-His-Arg-Gly-Tyr-Arg
SPM-MHb       His-Glu-Lys-His-His-Ser-His-Arg
SPM-MHc       His-Glu-Lys-His-His
```

| Protein or Peptide | Intensity of Fluorescence |
|---|---|
| Histatin 3 | + + + + |
| SPN-H3 | + |
| SPM-H3 | + + + + |
| SPC-H3 | - |
| Control 1 | - |
| Control 2 | - |

FIG. 8

AMINO ACID COMPOSITION OF MACAQUE AND HUMAN HISTATINS*

| Amino Acid | M-histatin 1 | | M-histatin 3 | | Histatin 1+ | | Histatin 3+ | |
|---|---|---|---|---|---|---|---|---|
| Asx | 3.5 | (4) | 1.3 | (1) | 5.2 | (5) | 4.4 | (4) |
| Ser | 2.8 | (3) | 1.2 | (1) | 2.6 | (3) | 2.8 | (3) |
| Glu | 3.3 | (3) | 1.8 | (2) | 3.2 | (3) | 0.8 | (1) |
| Pro | 0 | (0) | 0 | (0) | 1.1 | (1) | 0 | (0) |
| Gly | 4.2 | (4) | 2.6 | (3) | 3.2 | (3) | 2.3 | (2) |
| Ala | 0 | (0) | 0 | (0) | 0 | (0) | 0.9 | (1) |
| Leu | 1.1 | (1) | 0 | (0) | 1.1 | (1) | 1.1 | (1) |
| Tyr | 4.1 | (4) | 1.2 | (1) | 4.9 | (5) | 4.1 | (4) |
| Phe | 1.2 | (1) | 0.8 | (1) | 3.1 | (3) | 1.3 | (1) |
| His | 10.0 | (10) | 6.0 | (6) | 7.0 | (7) | 7.0 | (7) |
| Lys | 3.0 | (3) | 1.5 | (2) | 3.1 | (3) | 4.1 | (4) |
| Arg | 5.1 | (5) | 3.3 | (3) | 4.0 | (4) | 4.0 | (4) |
| Total: | 38.3 | (38) | 19.7 | (20) | 38.5 | (38) | 32.8 | (32) |

FIG. 9
Anti-Candidal Activities of Histatins and Histatin-Based Peptides

| | Amino Acid Sequence | Peptide Length (no. of amino acids) | Mole % | | | Activity (LD$_{50}$ or ID$_{50}$)* | | |
| --- | --- | --- | --- | --- | --- | --- | --- | --- |
| | | | His | Lys | Arg | Killing of Blastoconidia | Killing of Germinated Cells | Inhibition of Germination |
| Histatin-3 | 1-32 | 32 | 22 | 12 | 12 | 4.2 (±1.4) | 10.4 (±3.2) | 38.9 (±4.7) |
| SPM-H3 | 12-25 | 14 | 29 | 14 | 21 | 0.3 (±0.1) | 1.9 (±0.5) | 2.4 (±0.9) |
| 3P1 | 5-25 | 21 | 29 | 19 | 19 | 0.3 (±0.1) | 0.3 (±0.1) | 16.5 (±3.2) |
| 3P2 | 9-25 | 17 | 24 | 18 | 18 | 0.6 (±0.3) | 0.5 (±0.1) | >100 |
| 3P3 | 5-22 | 18 | 33 | 22 | 17 | 0.7 (±0.2) | 0.3 (±0.1) | 52.3 (±6.8) |
| 3P4 | 9-22 | 14 | 29 | 21 | 14 | 1.5 (±0.5) | 5.3 (±1.3) | >200 |
| 3P5 | 5-19 | 15 | 33 | 27 | 13 | 1.5 (±0.4) | 1.1 (±0.3) | >200 |
| M-Histatin 1 | 1-38 | 38 | 26 | 8 | 13 | 4.4 (±1.2) | 5.7 (±2.4) | 36.3 (±5.6) |
| SPM-MHa | 10-31 | 22 | 32 | 14 | 18 | 1.0 (±0.3) | 1.6 (±0.5) | 65.4 (±16.7) |
| SPM-MHb | 10-28 | 19 | 37 | 16 | 16 | 0.8 (±0.3) | 1.9 (±0.7) | 89.3 (±10.3) |
| SPM-MHc | 10-25 | 16 | 38 | 19 | 12 | 1.6 (±0.8) | 3.2 (±1.1) | 124.7 (±21.6) |

* Values indicate concentration of peptide or protein in nmoles per ml required for 50% killing (LD$_{50}$) or 50% inhibition (ID$_{50}$). Values in parentheses represent standard deviations. Each assay was performed in triplicate, and each experiment was repeated at least three times.

METHODS OF TREATING FUNGAL INFECTIONS USING HISTATIN-BASED PEPTIDES

This application is a division, of application Ser. No. 08/287,717 filed Aug. 9, 1994, now U.S. Pat. No. 5,986,503, which is a File Wrapper continuation of 08/145,030, filed Oct. 28, 1993, which is a File Wrapper continuation of 07/786,571, filed Nov. 1, 1991, both now abandoned.

GOVERNMENT SUPPORT

The invention described herein was supported in whole or in part by Grant No. DE07652 from the National Institutes of Health, which have certain rights in the invention.

BACKGROUND

Infection with the yeast *Candida albicans* is a prevalent and, in some cases, life-threatening condition affecting otherwise healthy and immuno-compromised patients. Candidal vaginitis is estimated to affect 15 to 55% of healthy young women. Candidal infections often occur in diabetics, during pregnancy, and following medication with antibiotics, steroid hormones, or oral contraceptives. (Tapper-Jones, L. M. et al. (1981) *J. Clin. Pathol.* 34:706-11; Sobel, J. D. et al. (1984) *Infect. Immun.* 44:576–580) Oral candidiasis is an early opportunistic infection of Acquired Immune Deficiency Syndrome (AIDS) in individuals infected with human immunodeficiency virus type 1, as well as a complication of radiation and chemotherapy in cancer patients. (Yeh, C. -K. et al. (1988) *J. of Acquired Immune Deficiency Syndromes* 1:361–366) In addition, candidal infection of denture wearers plays a primary role in dental stomatitis, a prevalent oral problem among the elderly. (Pollock, J. J. et al. (1990) *NYS Dental J.* 56:36–38) Candidal infections of skin and urethra are widespread problems. In patients in intensive care and immunocompromised patients, systemic fungal infection often leads to death, since there are few effective anti-fungal pharmaceuticals for intravenous use. (Burnie, J. P. et al. (1985) *British Medical Journal* 290:746–748)

Although several anti-fungal agents are currently available (e.g., clotrimazole, miconazole, ketoconazole, chlorhexidine, and nystatin), these are not completely effective and can produce adverse side effects. Many are not appropriate for oral or systemic administration. Thus, a potent, naturally occurring anti-fungal substance would provide a significant improvement in the treatment of fungal infection.

SUMMARY OF THE INVENTION

This invention is based on substantially pure peptides which have anti-candidal activity greater than that of intact, native histatins. These peptides represent defined portions of the amino acid sequences of naturally occurring human and macaque histidine-rich salivary proteins called histatins, and will be referred to herein as histatin-based peptides. As demonstrated herein, these histatin-based peptides have been shown to be superior in anti-candidal activity over the intact, native histatins. Thus, this invention provides compositions for treatment of fungal infection comprising histatin-based peptides with defined amino acid sequences. Compositions for anti-fungal treatment comprising substantially pure protein having the amino acid sequence of the naturally occurring macaque M-histatin 1 are also provided. Protein preparations of the macaque histatins, referred to herein as M-histatin 1, 2, 3, and 4, are also included. This invention further includes compositions for anti-fungal treatment comprising expression vectors encoding the histatin-based peptides. Compositions and methods for anti-fungal therapy using bacteria transformed with the above-mentioned expression vectors for expression of the encoded histatin(s) or histatin-based peptide(s) in the urinary/reproductive or gastrointestinal tract are also included. Proteins and peptides, expression vectors, transformed cells, and compositions and methods for treatment of fungal, and in particular, candidal infection using these substances are included within the scope of this invention.

BRIEF DESCRIPTION OF FIGURES

FIG. 1 shows the amino acid sequences of human histatin 3, SEQ ID NO: 1 and peptides SPM-H3 SEQ ID NO:2, 3P1, SEQ ID NO:3, 3P2, SEQ ID NO:4 3P3, SEQ ID NO:5, 3P4 SEQ ID NO:6, and 3P5 SEQ ID NO:7.

Table 1 shows the amino acid composition of macaque and human histatins. Values in parentheses were the residues identified by automated Edman degradation for M-histatin 1 and by amino acid analysis for M-histatin 3. +Data for these columns are from Oppenheim, F. G. et al. (1988) *J. Biol. Chem.* 263:7472–7477, which is herein incorporated by reference.

FIG. 5 shows the amino acid sequences of human histatins 1 SEQ ID NO:9 and 3 SEQ ID NO:1 compared with that of macaque M-histatin 1. SEQ ID NO:8. Dashed lines indicate gaps. Serines at residue 2 of M-histatin 1 and histatin 1 are phosphorylated. Residues in bold-face type indicate amino acid differences.

FIG. 6 shows the amino acid sequences of macaque M-histatin 1 SEQ ID NO:8 and peptides SPM-MHa SEQ ID NO:10, SPM-MHb SEQ ID NO:11, and SPM-MHc SEQ ID NO:12.

Table 2 shows the results of the anti-candidal assays for human histatin 3, histatin 3-based peptides, macaque M-histatin 1, and M-histatin 1-based peptides.

Figures 7A, 7B, 7C, 7D, 7E, 7F, 7G, 7H, 7I, 7J, 7K, 7L:
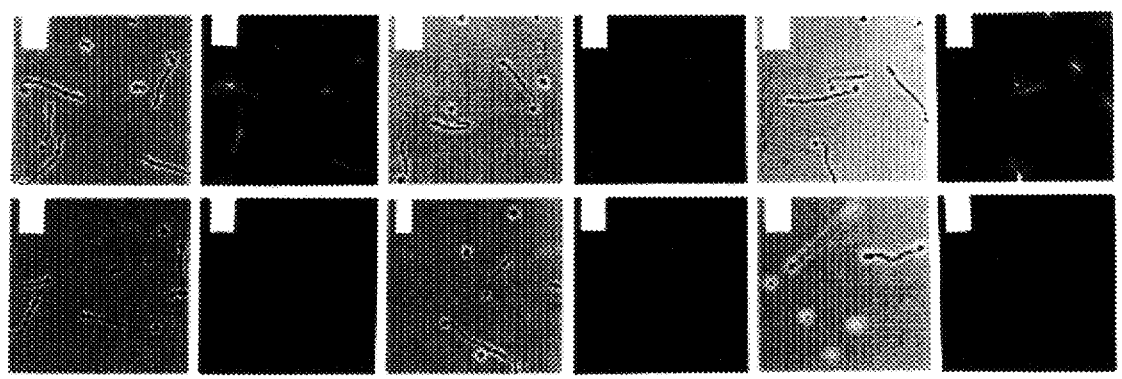

FIG. 7 shows the interaction of histatin 3 and histatin 3-based peptides with the cell surface of *C. albicans* by direct-fluorescence method. Above: Each pair of panels shows phase contrast/fluorescence microscopy, respectively, of: A/B Histatin 3; C/D SPN-H3; E/F SPM-H3; G/H SPC-H3; I/F Control 1; K/L Control 2. Below: Intensity of fluorescence was scored by inspection. ++++Heavy fluorescence; +++Moderate fluorescence; ++Definite fluorescence but minimal in amount; +Barely detectable fluorescence; and–No fluorescence.

DETAILED DESCRIPTION OF THE INVENTION

This invention relates to peptides which have anti-fungal activity, in which the amino acid sequences represent defined portions of the amino acid sequences of naturally occurring human and macaque histidine-rich salivary proteins called histatins. (Histatins are also referred to in the literature as histidine-rich proteins or HRPs.) Histatins are major salivary proteins which are synthesized in the parotid and submandibular-sublingual secretory glands of humans and Old World monkeys. (Azen, E. A. (1978) *Biochem. Genet.* 16:79–99) Histatins are believed to be part of an extraimmunologic defense system of the oral cavity. The anti-fungal activity of histatins, as well as their inhibitory effect on several oral bacteria (such as the cariogenic *Streptococcus mutans* and the periodontal *Porphyromonas gingivalis*), have been demonstrated in vitro. In addition, the observation that polyhistidine peptides inactivate herpes simplex virus in vitro and that whole saliva contains inhibitors of human immunodeficiency virus suggests the possibility that histatins may have anti-viral activity. These in vitro studies support potential clinical use of compositions containing histatins or histatin-based peptides for the treatment of local and systemic candidal infection, oral bacterial diseases, such as caries and periodontitis, and viral infection. (Pollock, J. J. et al. (1984) *Infect. Immun.* 44:702-7; Oppenheim, F. G. (1986) *J. Biol. Chem.* 261:1177-82; Iacono, V. J. et al. (1983) *J. Dent. Res.* 63:288; MacKay, B. J. et al. (1984) *Infect. Immun.* 44:695–701; Xu, T. et al. (1990) *J. Dent. Res.* 69:239; MacKay, B. J. et al. (1984) *J. Dent. Res.* 63:288; Oppenheim, F. G. et al. (1988). *J. Biol. Chem.* 263:7472–7477; Pollock, J. J. et al. (1985) In: *Protides of the Biological Fluids: Proceedings of the Colloquium* (H. Peeters, ed.), New York: Pergamon Press, Vol. 32, pp. 309–314; Docherty, J. J. et al. (1987) *Anti-microbial Agents and Chemotherapy* 31(10):1562–1566; Fox, P. C. et al. (1988) JADA 116:635–637; Nishikata, M. et al. (199i) *Biochem. Biophys. Res. Comm.* 174 (2): 625–630)

The human histatin proteins have been isolated and sequenced. They have been shown to be a family of twelve related low molecular weight proteins. Comparison of the amino acid sequences of the histatins suggests that histatin 2 and histatins 4–12 may have originated from specific proteolytic cleavage of histatin 1 and histatin 3, respectively. (Oppenheim, F. G. et al. (1988) *J. Biol. Chem.* 263:7472-77; Troxler, R. F. et al. (1990) *J. Dent. Res.* 69(1):2–6) Cloning and sequence analysis of histatin cDNAs further suggest that the histatins are encoded by two homologous genetic loci, whose primary products are histatins 1 and 3. (Sabatini, L. M. et al. (1989) *Biochem. Biophys. Res. Comm.* 160:495–502; Vanderspek, J. C. et al. (1990) *Arch. Oral Biol.* 35(2):137-43)

The amino acid sequences of the anti-fungal peptides of this invention represent defined portions of the amino acid sequence of human histatin 3 SEQ ID NO:1 (SPM-H3, SEQ ID NO:2, 3P1 SEQ ID NO:3, 3P2 SEQ ID NO:4, 3P4 SEQ ID NO:6, and 3P5SEQ ID NO:87), the complete amino acid sequence of macaque M-histatin 1 SEQ ID NO:7 protein, or defined portions of the amino acid sequence of M-histatin 1 (SPM-MHa SEQ ID NO:10, SPM-MHb SEQ ID NO:11, and SPM-MHc SEQ ID NO:12). This is the first time that the entire amino acid sequence of a nonhuman histatin protein is available. The peptides can be obtained from a naturally occurring source of histatin, or be produced (e.g., by recombinant DNA techniques or by chemical synthesis) to have the same, or substantially the same, amino acid sequence as all or a portion of the naturally occurring protein.

The peptides described herein were tested in three assays designed to measure separately their effectiveness in killing of blastoconidia, in killing of germinated cells, and in inhibition of germination of *C. albicans*. When tested in these assays, the histatin 3-based peptides and M-histatin 1-based peptides were found surprisingly to have superior anti-candidal activity over native, intact histatin 3 and M-histatin 1. In addition, peptides representing all or portions of the amino acid sequences of native histatins which have been modified by, for example, deletion, addition, substitution, or side chain modification of at least one referred to herein as modified histatin-based peptides. Isolated preparations of the macaque histatins, M-histatin 1, 2, 3, and 4, are also included in this invention.

The following is a description of the histatin-based peptides, the macaque histatins, the anti-fungal activities of the histatin-based peptides as measured in assays for killing of *Candida* blasto-conidia, killing of germinated cells, and inhibition of germination, and modified histatin-based peptides.

Histatin 3-Based Peptides

Histatin 3 was isolated from human parotid salivary secretions. The histatin 3-based peptides, SPM-H3, 3P1, 3P2, 3P3, 3P4, and 3P5, were chemically synthesized. The amino acid sequences of histatin 3 SEQ ID NO:1 and its derivative peptides SEQ ID NO:27 are shown in FIG. 1.

Isolation and Characterization of Macaque Histatins

Figure 2:
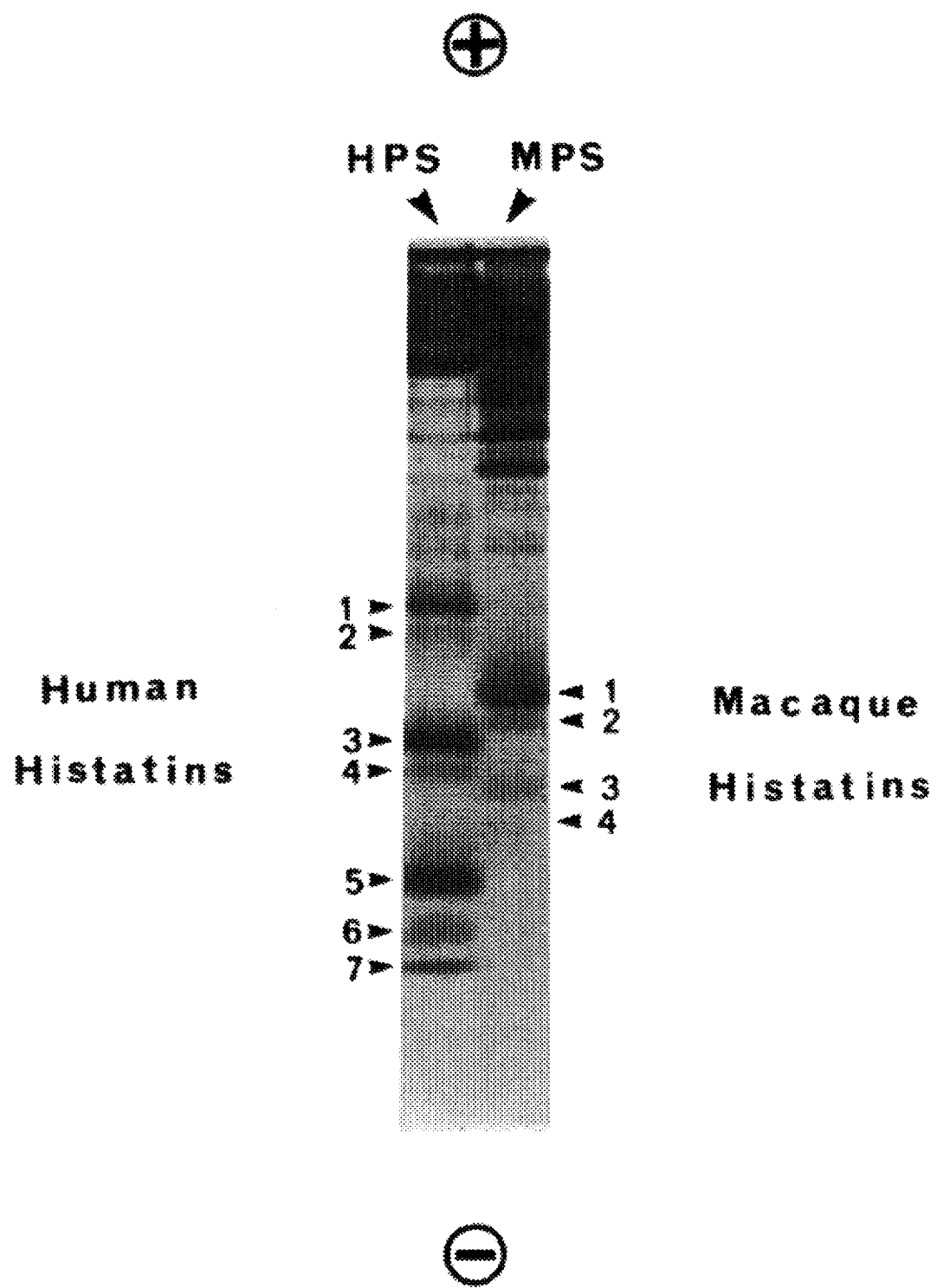
FIG. 2 shows the cationic PAGE electrophoretograms of human (HPS) and macaque (MPS) parotid saliva protein.

Comparison of the electrophoretic patterns of human and macaque (*Macaca fascicularis*) parotid salivary proteins in a cationic polyacrylamide gel electrophoresis (PAGE) system revealed the presence of one prominent protein band (M-histatin 1) with a mobility midway between those of human histatins 1 and 3 (FIG. 2). In addition, three minor bands were also noted (M-histatins 2, 3, and 4). M-histatin 2 was close to the major band, while M-histatins 3 and 4 represent a second pair of proteins migrating more cathodically and exhibiting mobilities midway between those of histatins 3 and 5.

Figure 3:
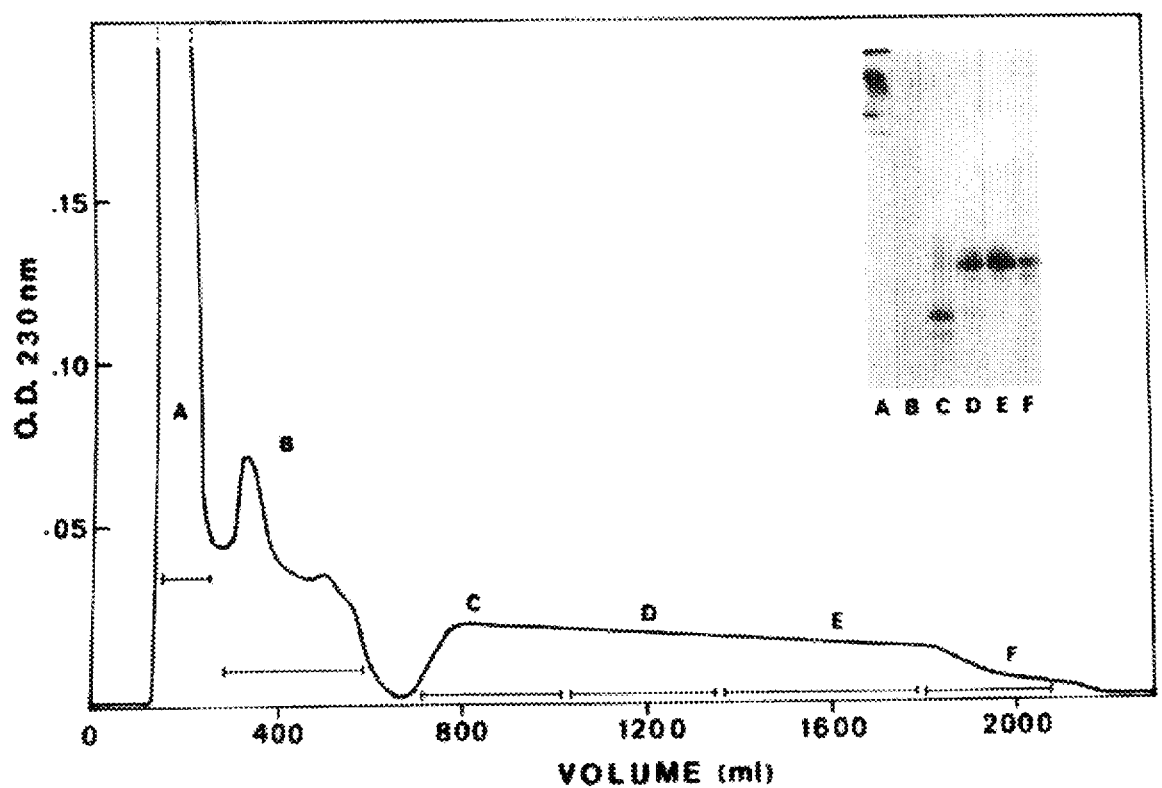
FIG. 3 shows the elution profile of *M. fascicularis* parotid saliva protein from a Bio-Gel P-2 column. Inset shows an aliquot of each fraction (A–F) examined in the cationic PAGE system.
Figure 4:
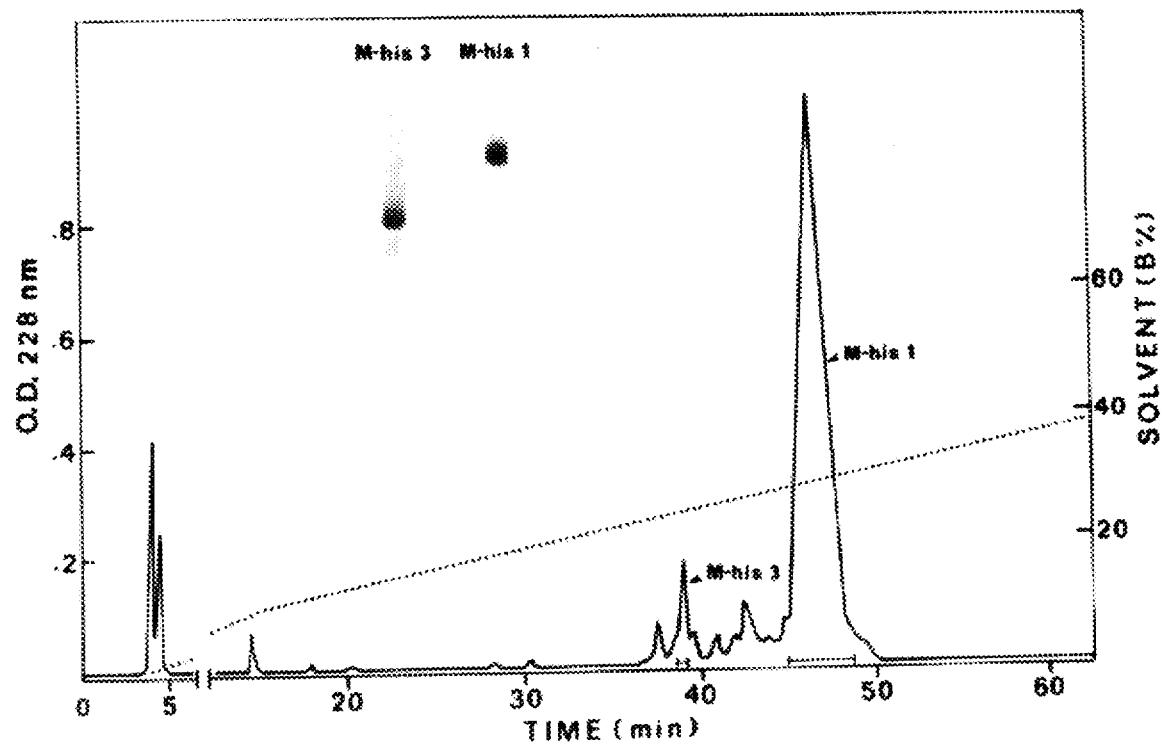
FIG. 4 shows the elution profile of fraction C–F during RP-HPLC chromatography. Inset shows purified preparations of M-histatin 1 and M-histatin 3 subjected to cationic PAGE.

Isolated preparations of M-histatins 1 and 3 were made, as illustrated in FIGS. 3 and 4. Isolation of M-histatin 2 and 4 proteins would follow essentially the same procedure.

The amino acid composition of M-histatin 1 and M-histatin 3 was compared with that of human histatins 1 and 3 in Table 1. M-histatin 1 contains ten residues of histidine, five of arginine, four of glycine and tyrosine, and three of aspartic acid/asparagine, glutamic acid/glutamine, serine, and lysine, and lacks threonine, proline, alanine, valine, cysteine, methionine, and isoleucine. The amino acid composition of M-histatin 3 is similar to that of M-histatin 1 in that it is enriched with respect to histidine, arginine, and glycine, but lacks leucine. The amino acid compositions of both M-histatins 1 and 3 are similar to those of human histatins 1 and 3, respectively.

The complete amino acid sequence of M-histatin 1 was determined SEQ ID NO:8. The protein has a pI of 8.5 and contains 38 amino acid residues. It has a molecular weight of 4881.8, with 26.3% consisting of histidine by weight. The hydropathicity plot of M-histatin 1 indicates that the molecule is hydrophilic along its entire length, and a prediction of secondary structure indicates that the molecule is devoid of alpha-helices and beta sheets, but instead contains a series of beta turns that would tend to give the protein a random structure in aqueous solutions. The experimentally determined sequence is in complete agreement with the amino acid composition of the protein (Table 1).

The amino acid composition of M-histatin 3 is nearly identical to that of the N-terminal 20 amino acid residues of M-histatin 1. This suggests that M-histatin 3 may arise from M-histatin 1 by chymotryptic-like cleavage between $Phe_{20}$ and $His_{21}$.

The primary structures of M-histatin 1 SEQ ID NO:8 and human histatins 1 SEQ ID NO:9 and 3 SEQ ID NO:1 were compared, with gaps introduced for delineation of inserts that are unique to one, but not the other, of these proteins (FIG. 5). M-histatin 1 contains a six-residue sequence, -Arg-His-Gly-His-His-Lys- (residues 10–15 SEQ ID NO:13), which is absent from histatins 1 and 3, and histatin 1 contains a hexapeptide sequence, -Phe-Pro-Phe-Tyr-Gly-Asp- (residues 24–29 SEQ ID NO:14), which is not present in either M-histatin 1 or histatin 3. Otherwise, these proteins are remarkably similar. M-histatin 1 and histatin 1 exhibit 89% sequence similarity, M-histatin 1 and histatin 3 exhibit 91% sequence similarity, and histatins 1 and 3 exhibit 88% sequence similarity, if the hexapeptide sequences unique to M-histatin 1 and histatin 1 SEQ. ID NO: 13 and 14, respectively, are not considered.

M-Histatin 1-Based Peptides

Peptides representing portions of the amino acid sequence of M-histatin 1 were chemically synthesized. The amino acid sequences of M-histatin 1 SEQ ID NO:8 and the M-histatin 1-based peptides, SPM-MHa SEQ ID NO:10, SPM-MHb SEQ ID NO:11, and SPM-MHc SEQ ID NO:12, are shown in FIG. 6.

Anti-Fungal Activities of Histatin 3 and M-Histatin 1 and Their Derivative Peptides C. albicans is a dimorphic yeast. It can exist in a yeast or blastoconidial form, which upon germination develops into the hyphal or germinated form. While the germinated form is considered to be more invasive, most of the C. albicans isolates harvested from the oral cavities of healthy individuals appear to be in the blastoconidial form. (Arendorf, T. M. et al. (1980) Arch. Oral Biol. 25:1–10; Gow, N. A. R. et al. (1987) Criti. Rev. Microbiol. 15:73–78; Odds, F. C. (1988) Candida and Candidosis, 2nd ed., Bailliere Tindall, London, England) Anti-fungal activity of histatin 3, M-histatin 1, and peptides based on portions of their amino acid sequences was measured in assays designed to test separately the effectiveness of the proteins against all developmental forms of Candida (Table 2). These assays, which measure killing of blastoconidia, killing of germinated cells, and inhibition of germination of C. albicans are described in Xu et al., which is herein incorporated by reference. (Xu, T. et al. (1991) Infect. Immun. 59(8):2549–2554). SPM-H3 was found to be about 5–10X more potent than histatin 3 in all three assays, demonstrating its superiority to the native, intact protein in both fungicidal and fungistatic activities. 3P1 and 3P3 were about 6–30X more potent than histatin 3 in the fungicidal activities, but had only about 1–2X the fungistatic activity of histatin 3. 3P2 had fungicidal activities similar to 3P1 and 3P3, but virtually no fungistatic activity. 3P4 was less potent than 3P1, 3P2, and 3P3 in fungicidal activities (about 2X more potent than histatin 3), and was also ineffective in inhibiting germination. 3P5, like 3P4, had about 2X the anti-fungal activity of histatin 3 in killing of biastoconidia and no fungistatic activity, but was about 5X more potent than 3P4 in killing of germinated cells.

Macaque M-histatin 1 was comparable in all three activities to human histatin 3. All three M-histatin 1-based peptides were about 2–5X more effective in fungicidal activities, but less potent in inhibition of germination than the intact macaque histatin. These results suggest that a combination of histatin-based peptides may be used for maximum anti-fungal activity against Candida in all three stages of its life cycle.

Comparison of the anti-candidal activities of the synthetic peptides within each group (histatin 3 or M-histatin 1) does not indicate a simple correlation between anti-fungal effectiveness, as measured by the three assays, and any single aspect of the primary structure of the peptides, that is, presence of N-terminal or C-terminal residues which may indicate functional domains, peptide length, or content of the basic amino acids, histidine, lysine, and arginine (Table 2). Thus, the anti-fungal potency of a histatin-based peptide seems to reside in a combination of the particular amino acid sequence and the length, that is, in the defined sequence of the peptide.

The mode by which histatins and histatin-based peptides exert their anti-fungal activity on C. albicans is suggested by preliminary results of a binding assay of labeled peptide portions of histatin 3 to Candida cells (FIG. 7). Synthetic peptides corresponding to the N-terminal portion (SPN-H3, residues 1–11), middle portion (SPM-H3, residues 12–25), and C-terminal portion (SPC-H3, residues 23–32) of the histatin 3 amino acid sequence were labeled with a fluorescent dye and incubated with Candida yeast and germinated forms. Binding was detected by fluorescence microscopy. Of the three peptide portions, only SPM-H3 bound significantly to Candida cells, and only SPM-H3 exhibited significant anti-candidal activity (Table 2). That the binding of SPM-H3 was specific was indicated by inhibition of binding of labeled SPM-H3 by preincubation of Candida cells with unlabeled SPM-H3. These results indicate that SPM-H3 interacts directly at the surface of Candida yeast and germinated cells.

Other Anti-Fungal Histatin-Based Peptides Including Modified Peptides

The analysis of the synthetic peptides suggests that optimization of the defined portion of the amino acid sequence of a naturally occurring histatin which gives maximal anti-fungal activity and optimization by modification of a histatin-based peptide are best done empirically. That is, peptides must be produced somewhat randomly and then tested in assays such as those described herein. Modified histatin-based peptides can differ from the corresponding naturally-occurring sequence by addition, deletion, substitution, or side-chain modification of at least one amino acid, or other chemical modification.

Peptide sequences containing permutations of the amino acid sequences of native histatins and modified peptides can be produced by known methods, such as recombinant DNA techniques and solid-phase synthesis. Cloned DNA encoding the human histatins may be obtained as described by Sabatini et al. or Vanderspek et al., whose teachings are incorporated herein by reference. (Sabatini. L. M. et al. (1989) Biochem. Biophys. Res. Comm. 160:495–502; Vanderspek, J. C. et al. (1990) Arch. Oral Biol. 35(2):137–43) cDNA encoding the macaque M-histatin 1 protein can be cloned by recombinant DNA techniques, for instance, by using degenerate oligonucleotides based on the amino acid sequence of the histatin as primers for polymerase chain reaction amplification. Alternatively, oligonucleotides encoding histatins or histatin-based peptides can be synthesized chemically using commercially available equipment. They can then be made double-stranded and cloned into vectors for amplification in prokaryotic or eukaryotic host cells.

Histatin-based peptides can be produced in a variety of expression vector/host systems, which are available commercially or can be reproduced according to recombinant DNA and cell culture techniques. The vector/host expression systems can be prokaryotic or eucaryotic, and can include bacterial, yeast, insect, mammalian, and viral expression systems. The construction of expression vectors encoding histatin-based peptides, transfer of the vectors into various host cells, and production of peptides from transformed host cells can be accomplished using genetic engineering techniques, as described in manuals such as *Molecular Cloning* and *Current Protocols in Molecular Biology*, whose teachings are incorporated herein by reference. (Sambrook, J., Fritsch, E. F. and Maniatis, T. (1989) *Molecular Cloning*, Second Edition, Cold Spring Harbor Laboratory Press; Ausubel, F. M. et al., eds., *Current Protocols in Molecular Biology*, New York: Greene Publishing Associates and Wiley-Interscience)

Modified histatin based peptides can be synthesized chemically, or be produced from cloned DNAs containing mutated nucleotide sequences. Histatin-based peptides encoded by expression vectors may be modified due to post-translational processing in a particular expression vector/host cell system. (See, e.g., Wold, F. (1981) *Ann. Rev. Biochem.* 50:783–814) Histatin-based peptides may also be modified by chemical alteration of amino acid side-chain groups, or by other covalent modification. (See, e.g., Glazer, A. N. et al. (1975) *Chemical Modification of Proteins*, North Holland; Katre, N. V. et al. (1987) *Proc. Natl. Acad. Sci. USA* 84:1487)

Therapeutic Applications

The histatin-based peptides of this invention, representing defined portions of the amino acid sequence of human histatin 3 SEQ. ID NO: 1 SPM-H3 SEQ. ID NO: 2 3P1, SEQ ID NO: 3 3P2, SEQ ID NO: 4, 3P3 SEQ ID NO:5 3P4 SEQ ID NO:6, and 3P5 SEQ ID NO:7, or all or defined portions of the amino acid sequence of M-histatin 1: M-histatin 1, SPM-MHa SEQ ID NO:10, SPM-MHb SEQ ID NO:11, and SPM-MHc SEQ ID NO: 12, can be used in compositions and methods of treatment for fungal, and in particular, candidal infection. These methods of treatment for fungal infection apply to preventive treatment as well. The compositions may contain combinations of histatin-based peptides, in order to obtain maximum activity against all developmental forms of *Candida*. The ionic strength, presence of various mono- and divalent ions, and pH of the compositions may be adjusted to obtain maximum anti-fungal activity of the histatin-based peptides, as described in Xu et al. (Xu, T. et al. (1991) *Infect. Immun.* 59(8):2549-54) Carriers appropriate for administration of anti-fungal agents to the vagina, the urethra, the oral cavity, and skin are known, and described, for instance, in U.S. Pat. No. 4,725,576 (Fungicidal Polypeptide Compositions Containing L-His and Methods for Use Therefore by J. J. Pollock and B. J. MacKay, Feb. 16, 1988). Compositions for treatment of systemic infection can be administered by various routes, such as intravenously or subdermally.

Expression vectors encoding the above-mentioned peptides can be used in compositions and methods for anti-fungal treatment. Expression vectors may be administered in compositions which introduce genetic material encoding histatin-based peptides into cells of the patients. For example, recombinant expression vectors based on retroviruses or adenovirus vaccines may be used to infect patients.

A method of anti-fungal therapy using the above-described expression vectors is bacterial substitution therapy. Bacterial substitution therapy can be used to treat fungal infection of areas in the urinary/reproductive and/or gastrointestinal tracts of a patient. The therapy comprises the following: 1) transforming bacteria with DNA comprising an expression vector which encodes a histatin-based peptide described above, thereby producing transformed cells; 2) selecting transformed cells which express the peptide encoded by the expression vector, thereby obtaining tranformed cells which express a histatin-based peptide; and 3) administering transformed cells which express a histatin-based peptide in an appropriate carrier to the infected area.

One application of bacterial substitution therapy is treatment of fungal infections of the oral cavity. A number of species of the oral bacterial *Streptococcus* can be used as vehicles for the expression vectors. For example, recombinant *S. lactis* has been used in oral immunization of mice against a heterologous antigen. (Iwaki, M. et al. (1990) *Infect. Immun.* 58(9):2929-34) Other oral bacteria which can be used as vehicles for the expression vectors, plasmids for constructing expression vectors capable of amplification in oral bacterial host cells, transformation methods, and administration of compositions containing oral bacteria to humans have been described. (See, e.g., Kuramitsu, H. K. et al. (1984) *J. General Microbiology* 130:2497–2500; LeBlanc, D. J. et al. (1978) *Proc. Natl. Acad. Sci. USA* 75(7):3484–3487; Macrina, F. L. et al. (1980) *J. Bacteriology* 143(3):1425–1435; Kuramitsu, H. K. et al. (1982) *Infect. Immun.* 36(1):435–436; Svanberg, M. et al. (1984) *Infect. Immun.* 43(3):817–821).

The compositions and methods for treatment of fungal infections discussed above are not limited to use in humans, but can have veterinary applications as well.

Furthermore, the above-described compositions and methods for treatment of fungal infection can also be used for treatment of bacterial infections (e.g., of *S. mutans* or *P. gingivalis*) and viral infections (e.g., of herpex simplex virus or human immunodeficiency virus type 1).

Examples

1. Chemical synthesis of Histatin-Based Peptides

Isolation and amino acid sequence of human histatin 3 SEQ ID NO: 1 are described in Oppenheim et al., whose teachings are herein incorporated by reference. (Oppenheim, F. G. et al. (1988) *J. Biol. Chem.* 263(16):7472–7477) Human and macaque histatin-based peptides were synthesized by the solid phase method of Merrifield. (Merrifield, B. (1986.) *Science* 232:341-47) Peptides were synthesized by a MilliGen/Bioresearch Sam-Two Peptide Synthesizer using Fmoc L-amino acid kits (Millipore, Bedford, Mass.) and purified on a TSK ODS-120T $C_{18}$ column (5 µm, 4.6×250 mm) using RP-HPLC (Pharmacia-LKB). The purified peptides were quantified by amino acid analysis on a Beckman System 6300 amino acid analyzer.

3. Candida Binding Assay

Histatin 3 and synthetic peptides were labeled with a fluorochrome (5-(and 6)-carboxyfluorescein, succinimidyl ester) (Molecular Probes, Eugene, Or.) according to the method of Forni and Perters. (Forni, L. and Perters, S. (1984) *Methods Enzymol.* 108:413–425) Several modifications have been made. Briefly, histatin and peptides in 0.1M sodium bicarbonate buffer (pH 9.0) were incubated with the fluorochrome (freshly prepared in dimethyl sulfoxide) for 24 hours at 4° C. in the dark, respectively. Reaction was stopped by adding 50 mM glycine in 0.1M Tris-HCl and incubated for 3 hours at 4° C. in the dark. The conjugated-protein/peptide was separated from unbound dye and free protein/peptides by RP-HPLC. The amount of the conjugates was determined by amino acid analysis. The initial protein/peptide vs. fluorochrome dye ratio was 1:8 (μmol/ μmol). The conjugate percentage was about 90% by using the modified method.

*C. albicans* ($2 \times 10^7$ cells/ml, in PBS) in yeast or germinated forms were incubated with conjugated histatin or peptides (0.5–1.0 nmol/ml concentration) for 30 minutes at 25° C. in 1.5 ml test tubes, respectively. The tubes were centrifuged three times at 1000 g for 5 minutes. After discarding the supernatant, the tubes were refilled with 1 ml PBS to suspend the cell pellet. Cell suspension (200 μl) was added into a chamber slide and incubated at 25° C. for 30 minutes in the dark. After washing with PBS and removal of the chamber, the slide was mounted, observed (at 450–490 nm) and photographed as described above. The controls were processed with unconjugated protein/peptides (0.5–1.0 nmol/ml) and fluorochrome (2 μg/ml), respectively.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A method for treating fungal infection comprising administering a composition comprising a substantially pure peptide having an amino acid sequence selected from the group consisting of:
a) the amino acid sequence of SPM-H3 as set forth in SEQ ID NO: 2;
b) the amino acid sequence of 3P1 as set forth in SEQ ID NO: 3;
c) the amino acid sequence of 3P2 as set forth in SEQ ID NO: 4;
d) the amino acid sequence of 3P3 as set forth in SEQ ID NO: 5;
e) the amino acid sequence of 3P4 as set forth in SEQ ID NO: 6;
f) the amino acid sequence of 3P5 as set forth in SEQ ID No: 7;
g) the amino acid sequence of M-histatin 1 as set forth in SEQ ID NO: 8;
h) the amino acid sequence of SPM-MHa as set forth in SEQ ID NO: 10;
i) the amino acid sequence of SPM-MHb as set forth in SEQ ID NO: 11;
j) the amino acid sequence of SPM-MHc as set forth in SEQ ID NO: 12; and
k) combinations of two or more of the above.

2. A method for treating candidal infection comprising administering a composition of claim 1.

3. A method for treating fungal infection comprising administering a composition of claim 1, wherein the fungal infection is an infection selected from the group consisting of:

a) an infection of the oral cavity;

b) an infection of the vagina;

c) an infection of the urethra;

d) an infection of the skin; and e) a systemic infection.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Asp Ser His Ala Lys Arg His His Gly Tyr Lys Arg Lys Phe His Glu
 1               5                  10                  15
Lys His His Ser His Arg Gly Tyr Arg Ser Asn Tyr Leu Tyr Asp Asn
                20                  25                  30
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Arg Lys Phe His Glu Lys His His Ser His Arg Gly Tyr Arg
 1               5                  10
```

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Lys Arg His His Gly Tyr Lys Arg Lys Phe His Glu Lys His His Ser
 1               5                  10                  15
His Arg Gly Tyr Arg
                20
```

( 2 ) INFORMATION FOR SEQ ID NO:4:

( i ) SEQUENCE CHARACTERISTICS:
        ( A ) LENGTH: 17 amino acids
        ( B ) TYPE: amino acid (D) TOPOLOGY: linear (ii) MOLECULE TYPE: peptide (xi) SEQUENCE DESCRIPTION: SEQ ID NO:4:

```
Gly Tyr Lys Arg Lys Phe His Glu Lys His His Ser His Arg Gly Tyr
1               5                   10                  15
Arg
```

(2) INFORMATION FOR SEQ ID NO:5:

(i) SEQUENCE CHARACTERISTICS:
(A) LENGTH: 18 amino acids
(B) TYPE: amino acid
(D) TOPOLOGY: linear (ii) MOLECULE TYPE: peptide (xi) SEQUENCE DESCRIPTION: SEQ ID NO:5:

```
Lys Arg His His Gly Tyr Lys Arg Lys Phe His Glu Lys His His Ser
1               5                   10                  15
His Arg
```

(2) INFORMATION FOR SEQ ID NO:6:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:6:

```
Gly Tyr Lys Arg Lys Phe His Glu Lys His His Ser His Arg
1               5                   10
```

(2) INFORMATION FOR SEQ ID NO:7:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO:7:

```
Lys Arg His His Gly Tyr Lys Arg Lys Phe His Glu Lys His His
1               5                   10                  15
```

(2) INFORMATION FOR SEQ ID NO:8:

(i) SEQUENCE CHARACTERISTICS:
(A) LENGTH: 38 amino acids
(B) TYPE: amino acid
(D) TOPOLOGY: linear (ii) MOLECULE TYPE: protein (xi) SEQUENCE DESCRIPTION: SEQ ID NO:8:

```
Asp Ser His Glu Glu Arg His His Gly Arg His Gly His His Lys Tyr
1               5                   10                  15
Gly Arg Lys Phe His Glu Lys His His Ser His Arg Gly Tyr Arg Ser
                20                  25                  30
Asn Tyr Leu Tyr Asp Asn
                35
```

( 2 ) INFORMATION FOR SEQ ID NO:9:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Asp Ser His Glu Lys Arg His His Gly Tyr Arg Arg Lys Phe His Glu
1               5                   10                  15

Lys His His Ser His Arg Glu Phe Pro Phe Tyr Gly Asp Tyr Gly Ser
            20                  25                  30

Asn Tyr Leu Tyr Asp Asn
            35
```

( 2 ) INFORMATION FOR SEQ ID NO:10:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Arg His Gly His His Lys Tyr Gly Arg Lys Phe His Glu Lys His His
1               5                   10                  15

Ser His Arg Gly Tyr Arg
            20
```

( 2 ) INFORMATION FOR SEQ ID NO:11:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Arg His Gly His His Lys Tyr Gly Arg Lys Phe His Glu Lys His His
1               5                   10                  15

Ser His Arg
```

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Arg His Gly His His Lys Tyr Gly Arg Lys Phe His Glu Lys His His
1               5                   10                  15
```

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Arg His Gly His His Lys
1               5

( 2 ) INFORMATION FOR SEQ ID NO:14:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:14:

Phe Pro Phe Tyr Gly Asp
1               5